US010584390B2

(12) United States Patent
Bounpheng et al.

(10) Patent No.: US 10,584,390 B2
(45) Date of Patent: Mar. 10, 2020

(54) TRITRICHOMONAS FOETUS NUCLEIC ACID DETECTION METHODS

(71) Applicant: THE TEXAS A&M UNIVERSITY SYSTEM, College Station, TX (US)

(72) Inventors: Mangkey A. Bounpheng, Austin, TX (US); Thomas B. Hairgrove, Bryan, TX (US); Carly C. Summarell, Houston, TX (US); Megan E. Schroeder, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 246 days.

(21) Appl. No.: 15/501,222

(22) PCT Filed: Aug. 6, 2015

(86) PCT No.: PCT/US2015/043915
§ 371 (c)(1),
(2) Date: Feb. 2, 2017

(87) PCT Pub. No.: WO2016/022747
PCT Pub. Date: Feb. 11, 2016

(65) Prior Publication Data
US 2017/0233830 A1    Aug. 17, 2017

Related U.S. Application Data

(60) Provisional application No. 62/033,893, filed on Aug. 6, 2014.

(51) Int. Cl.
| | | |
|---|---|---|
| *C12Q 1/6893* | (2018.01) | |
| *C12Q 1/6851* | (2018.01) | |
| *C12Q 1/6888* | (2018.01) | |
| *C07H 21/04* | (2006.01) | |

(52) U.S. Cl.
CPC ......... *C12Q 1/6893* (2013.01); *C12Q 1/6851* (2013.01); *C12Q 1/6888* (2013.01); *C12Q 2600/158* (2013.01)

(58) Field of Classification Search
None
See application file for complete search history.

(56) References Cited

U.S. PATENT DOCUMENTS

| 7,674,752 B2 | 3/2010 | He et al. |
| 8,039,269 B2 | 10/2011 | Maerkl et al. |

OTHER PUBLICATIONS

Hartman et al., "Development of a novel internal positive control for Taqman based assays," Molecular and Cellular Probes, vol. 19, pp. 51-59. (Year: 2005).*

McMillen et al., "Improved detection of *Tritrichomonas foetus* in bovine diagnostic specimens using a novel probe-based real time PCR assay," Veterinary Parasitology, vol. 141, pp. 204-215. (Year: 2006).*

Schroeder et al., "Development and performance evaluation of calf diarrhea pathogen nucleic acid purification and detection workflow", Journal of Veterinary Diagnostic Investigation, vol. 24, No. 5, pp. 945-953. (Year: 2012).*

Bondurant, R. H. et al. "Detection of *Tritrichomonas foetus* by polymerase chain reaction in cultured isolates, cervicovaginal mucus, and formalin-fixed tissues from infected heifers and fetuses" *Journal of Veterinary Diagnostic Investigation*, Nov. 2003, pp. 579-584, vol. 15.

Effinger, L. et al. "Pooling of cultured samples and comparison of multistate laboratory workflows with the MagMAX sample preparation system and VetMAX quantitative polymerase chain reaction reagents for detection of *Tritrichomonas foetus*—colonized bulls" *Journal of Veterinary Diagnostic Investigation*, 2014, pp. 72-87, vol. 26, No. 1.

Schroeder, M. E. et al. "Development and performance evaluation of a streamlined method for nucleic acid purification, denaturation, and multiplex detection of Bluetongue virus and Epizootic hemorrhagic disease virus" *Journal of Veterinary Diagnostic Investigation*, 2013, pp. 1-11.

Thermofisher.com, "VetMAX—Plus qPCR Master Mix" *Applied Biosystems*, retrieved on Jan. 26, 2017 from the internet, URL: http://tools.thermofisher.com/content/sfs/manuals/cms_063759.pdf, Sep. 10, 2010, pp. 1-19.

Written Opinion in International Application No. PCT/US2015/43915, dated Nov. 24, 2015, pp. 1-5.

Guerra, A. G. et al. "Sensitivity of a real-time polymerase chain reaction for *Tritrichomonas fetus* in direct individual and pooled preputial samples" *Theriogenology*, 2013, pp. 1097-1103, vol. 80.

Guerra, A. G. et al. "Use of pooled protozoal cultures of preputial scraping samples obtained from bulls for the detection of *Tritrichomonas foetus* by means of a real-time polymerase chain reaction assay" *JAVMA*, Feb. 1, 2014, pp. 352-356, vol. 244, No. 3.

McMillen, L. et al. "Improved detection of *Tritrichomonas foetus* in bovine diagnostic specimens using a novel probe-based real time PCR assay" *Veterinary Parasitology*, 2006, pp. 204-215, vol. 141.

Ondrak, J. D. et al. "Repeated testing by use of culture and PCR assay to detect *Tritrichomonas foetus*, carrier bulls in an infected Nebraska herd" *JAVMA*, Nov. 1, 2010, pp. 1068-1073, vol. 237, No. 9.

Schroeder, M. E. et al. "Development and performance evaluation of calf diarrhea pathogen nucleic acid purification and detection workflow" *Journal of Veterinary Diagnostic Investigation*, 2012, pp. 945-953, vol. 24, No. 5.

Wilson, W. C. et al. "Development of a Rift Valley fever real-time RT-PCR assay that can detect all three genome segments" *Journal of Virological Methods*, 2014, pp. 426-431, vol. 193.

(Continued)

*Primary Examiner* — Young J Kim
(74) *Attorney, Agent, or Firm* — Saliwanchik, Lloyd & Eisenschenk

(57) ABSTRACT

The present invention provides quantitative polymerase chain reaction (PCR) methods and kits for diagnosing trichomoniasis.

20 Claims, 6 Drawing Sheets

Specification includes a Sequence Listing.

(56) References Cited

OTHER PUBLICATIONS

Bounpheng, M. A. et al. Comparison of DNA Purification and Detection Workflows for *Tritrichomonas foetus* Detection [online], American Association of Veterinary Laboratory Diagnosticians, AAVLD Annual Conference Proceedings, Nov. 2010 [retrieved on Oct. 19, 2015], retrieved from Internet, http://www.aavld.org/assets/documents/FINAL%20FROM%20PRINTER_10-26-10.pdf, pp. 1-278, see p. 151.

* cited by examiner

TRITRICHOMONAS FOETUS NUCLEIC ACID DETECTION METHODS

CROSS-REFERENCE TO RELATED APPLICATIONS

This application is the U.S. national stage application of International Patent Application No. PCT/US2015/043915, filed Aug. 6, 2015, which claims the benefit of U.S. Provisional Application Ser. No. 62/033,893, filed Aug. 6, 2014, the disclosures of which are hereby incorporated by reference in their entirety, including all figures, tables and amino acid or nucleic acid sequences.

The Sequence Listing for this application is labeled "Seq-List.txt" which was created on Aug. 4, 2015 and is 7 KB. The entire contents of the sequence listing is incorporated herein by reference in its entirety.

BACKGROUND OF THE INVENTION

Bovine trichomoniasis (BT) is a venereal disease of cattle caused by the single-cell protozoan *Tritrichomonas foetus* (*T. foetus*). *T. foetus* has long been recognized as a serious reproductive disease in cattle. *T. foetus* colonizes the epithelial surfaces of the bovine reproductive tract, causing inflammation, embryonic losses, and infertility in cows. Infection in bulls is typically asymptomatic and restricted to the epithelial surface of the penis, prepuce and urethra. Infected bulls become inapparent carriers of the organism and serve as the predominate reservoir of *T. foetus* in cattle populations. Coitus between carrier bulls and susceptible cows or heifers is the main route of transmission. Consequently, *T. foetus* causes serious economic losses where natural breeding conditions exist, due to reduced calf crops and culling of infected cattle. The direct cost to the Texas cow-calf sector is estimated to be $300-million per year (Anderson and Hairgrove). BT has become a reportable disease in Texas with control efforts mainly focusing on mandatory testing of breeding bulls and culling of infected animals.

Approved testing methods for *T. foetus* include a culture test that requires daily microscopic examination for up to six days and nucleic acid detection by PCR. For both methods, smegma samples are collected into a culture media pouch (InPouch containing ~3.7 ml, approx. $5/pouch) and incubated at ~37° C. for at least 48 hours (PCR) and up to 6 days (microscopic examination). For PCR, ~300 μl of InPouch sample is used for nucleic acid purification and *T. foetus* DNA (5.8 S ribosomal RNA (rRNA) gene) detection.

BRIEF SUMMARY OF THE INVENTION

Aspects of the present invention provide quantitative polymerase chain reaction (qPCR) methods for diagnosing trichomoniasis in a subject sample. In various embodiments, methods for diagnosing trichomoniasis in a subject sample are performed by extracting nucleic acids from a cell fraction from the sample; carrying out a qPCR on the nucleic acids with a primer set comprising a forward primer and a reverse primer, wherein the primer set permits the generation of a PCR amplicon that includes a region of a *Tritrichomonas* spp. gene or a *Trichomonas* spp. gene; and detecting the PCR amplicon; wherein the presence of the amplicon indicates a positive diagnosis of trichomoniasis in the subject sample. In some embodiments, the PCR amplicon detection step further includes hybridizing a probe to the amplicon. In various embodiments of this aspect of the invention, the sample is not cultured prior to the extraction of nucleic acids from the sample. Various PCR formats are amenable to use in the instantly claimed invention, including the reverse transcription quantitative real-time polymerase chain reaction (RT-qPCR).

Aspects of the invention also provide for kits for the detection of *Tritrichomonas* spp. and *Trichomonas* spp. In various embodiments, kits for the detection of *Tritrichomonas* spp. or *Trichomonas* spp. comprise a primer set comprising a forward primer and a reverse primer, wherein the forward primer and the reverse primer are capable of generating a PCR amplicon from a region of one or more *Tritrichomonas* spp. gene(s) or one or more *Trichomonas* spp. gene(s); and a probe capable of hybridizing to the PCR amplicon. In some embodiments, the kits further comprise an exogenous internal positive control polynucleotide and the respective internal positive control primer set comprising a control forward primer and a control reverse primer, wherein the control forward primer and the control reverse primer are capable of generating a control PCR amplicon from the exogenous internal positive control polynucleotide.

DETAILED DISCLOSURE OF THE INVENTION

Figure 1:
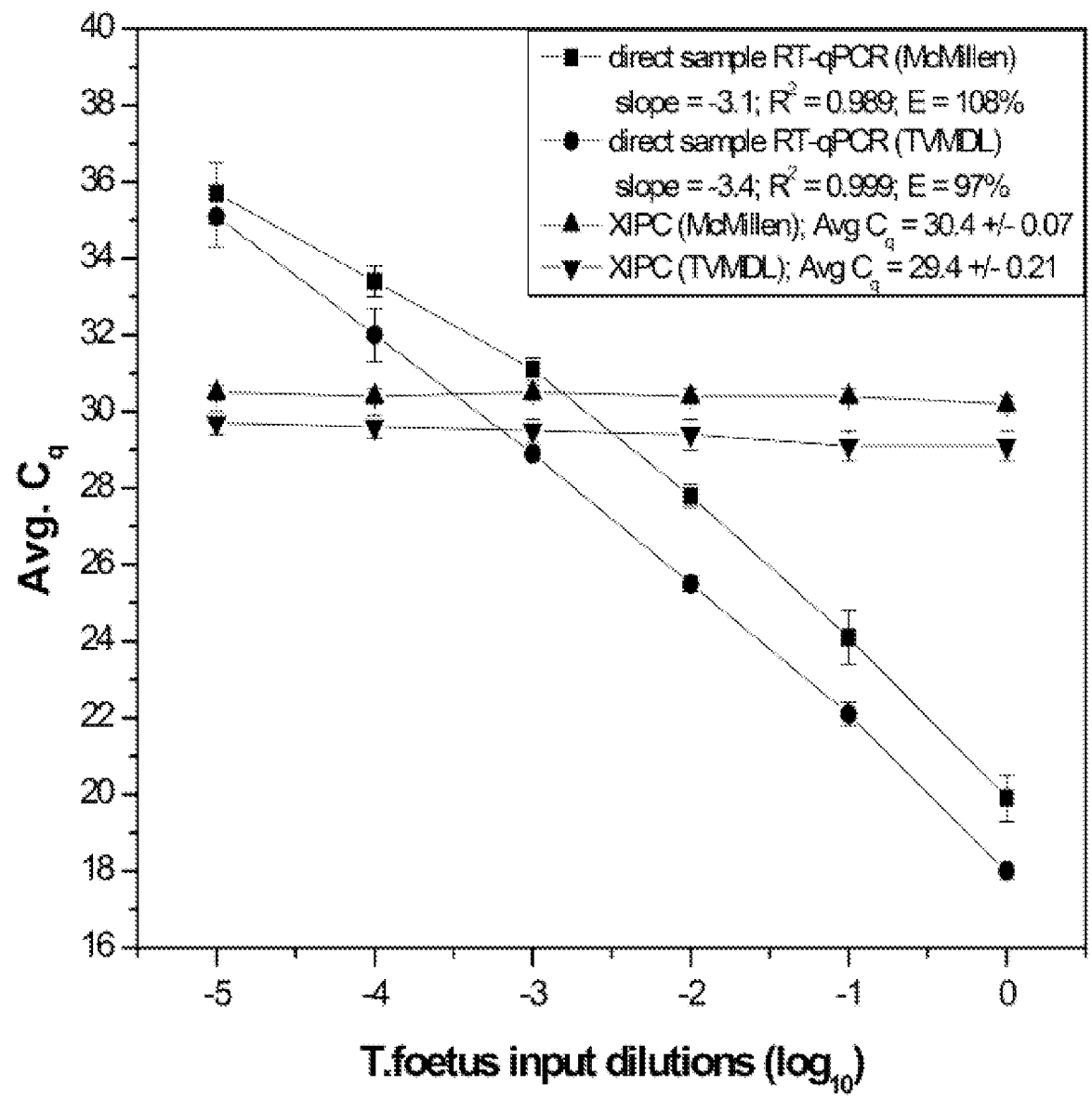
FIG. 1. *T. foetus* organism input serial dilutions, spanning five log dynamic range, were used for nucleic acid purification and detection RT-qPCR; 10,000 copies of XIPC RNA was spiked into each nucleic acid purification. Each input dilution was tested 12 times, thus each data point is the average of 12 nucleic acid purification and RT-qPCR; RT-qPCR $C_q$ values utilizing McMillen and TVMDL assays/oligos are provided.

Before the present methods and kits for detection and diagnosis of trichomoniasis are disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an" and "the" include plural referents unless the content clearly dictates otherwise. Additionally, the terms "comprising", "consisting of" and "consisting essentially of" are defined according to their standard meaning. The terms may be substituted for one another throughout the instant application in order to attach the specific meaning associated with each term.

In describing and claiming the present invention, the following terminology will be used in accordance with the definitions set out below.

As used herein, the term "subject" refers to an animal. Typically, the terms "subject" and "patient" may be used interchangeably herein in reference to a subject. As such, a "subject" includes an animal that is being tested for, and is capable of being infected by, organisms that cause trichomoniasis. The term "animal," includes, but is not limited to non-human animals such as cattle, canines, and felines. In some embodiments, humans can be tested as disclosed herein.

As used herein, the term "sample" can be any tissue, cell, fluid, or other source of nucleic acids from a subject.

The term "amplicon" as used herein refers to the DNA sequence generated by a RT-qPCR reaction. "Amplicon" may be used interchangeably with the term "PCR product."

Aspects of the present invention provide PCR methods, including (but not limited to reverse transcription quantitative real-time polymerase chain reaction (RT-qPCR) methods) for diagnosing trichomoniasis in a subject sample. In various embodiments, methods for diagnosing trichomoniasis in a subject sample are performed by extracting nucleic acids from a cell fraction from the sample; carrying out a qPCR (or RT-qPCR) on the nucleic acids with a primer set comprising a forward primer and a reverse primer, wherein the primer set permits the generation of a PCR amplicon that includes a region of a *Tritrichomonas* spp. gene or a *Trichomonas* spp. gene; and detecting the PCR amplicon; wherein the presence of the amplicon indicates a positive diagnosis of trichomoniasis in the subject sample. In various embodiments of this aspect of the invention, the sample is not cultured prior to the extraction of nucleic acids from the sample.

RT-qPCR targeting the coding expressed genes that are present in higher copies than the respective gene has not been reported for *T. foetus* nor *T. vaginalis*. Conventional detection of these pathogens targets the genomic DNA sequence. The current widely utilized qPCR *T. foetus* detection method targets the DNA of the *T. foetus* organism, specifically the 5.8 S rRNA gene (DNA) (McMillen and Lew, 2006; Ondrak et al., 2010; Garcia Guerra et al., 2013; Effinger et al., 2014; Garcia Guerra et al., 2014). The 5.8 S rRNA gene (DNA) is highly repetitive (100-2000 copies per cell; Nobelprize.org, 2013), which provides multiple DNA targets per cell thus potentially enabling higher sensitivity than lower copy number targets. Consequently, transcription of this gene by RNA polymerase results in a high number of copies of 5.8 S rRNA (up to 20,000 copies per cell; Nobelprize.org, 2013). By detecting the RNA, greatly improved target detection sensitivity is enabled. To our knowledge, targeting the coding expressed genes (RNA) that are present in higher copies than the respective gene has not been reported for *T. foetus*. Conventional detection of *T. foetus* targets the DNA sequence, however, by using single-step reverse transcriptase PCR, RNA and DNA can be targeted in the same reaction. Using the purified nucleic acid (purNA) consisting of RNA and DNA from smegma, the reverse transcriptase will produce complementary DNA (cDNA) using RNA as template. Subsequently, the cDNA and DNA that is present in the purNA are amplified by DNA polymerase. However, by using single step reverse transcriptase PCR that contains both reverse transcriptase and DNA polymerase in the same tube/reaction, RNA and DNA can be targeted concurrently in the same reaction.

Aspects of the invention also provide for kits for the detection of *Tritrichomonas* spp. and *Trichomonas* spp. In various embodiments, kits for the detection of *Tritrichomonas* spp. or *Trichomonas* spp. comprise a primer set comprising a forward primer and a reverse primer, wherein the forward primer and the reverse primer are capable of generating a PCR amplicon from a region of one or more *Tritrichomonas* spp. gene(s) or one or more *Trichomonas* spp. gene(s); and a probe capable of hybridizing to the PCR amplicon. In some embodiments, the probe comprises the nucleotide sequence of 5'-ACAAGTTCGATCTTTG-3' (SEQ ID NO:5) or 5'-ATCTTTGAATGCACATT-GCGCGCC-3' (SEQ ID NO:6).

In some embodiments, the methods and kits further comprise an exogenous internal positive control polynucleotide and the respective internal positive control primer set comprising a control forward primer and a control reverse primer, wherein the control forward primer and the control reverse primer are capable of generating a control PCR amplicon from the exogenous internal positive control polynucleotide. In some embodiments, exogenous internal positive control polynucleotide is a universal exogenous internal positive control (XIPC) comprises the nucleotide sequence of SEQ ID NO:7 (RNA) or SEQ ID NO:8 (DNA). XIPC RNA, which contains noninfectious unique artificial antigenomic sequence (GenBank Accession DQ883679) and possess no significant homology to the current annotated public sequences data, can serve as a universal internal positive control for diverse quantitative PCR assays. The XIPC ensures that a true negative result is due to lack of target nucleic acid as opposed to a false negative result due to the absence of target (due to a non-functional nucleic acid purification process) or presence of PCR inhibitors. The XIPC RNA can be used for both nucleic acid purification and amplification internal controls. The use of XIPC has been reported in (Schroeder et al., *JVDI*, 2013; Wilson et al., *J. Virol. Med.*, 2013; and Schroeder et al., *JVDI*, 2012). The control forward primer can comprise the nucleotide sequence of 5'-TTCGGCGTGTTATGCTAACTTC-3' (SEQ ID NO:9) and the control reverse primer can comprise the nucleotide sequence of 5'-CCACTGCGCCCAACCTT-3' (SEQ ID NO:10).

In some embodiments, the sample is a smegma sample, and can be collected from any mammal, such as, but not limited to, bovine, felines, canines, and humans. In such embodiments, the PCR amplicon that includes a region of one or more *Tritrichomonas* spp. gene(s) or one or more *Trichomonas* spp. gene(s) is generated in the presence of the animal's endogenous nucleic acids during the PCR or RT-qPCR. As discussed above, various embodiments of this aspect of the invention provide for the use of a sample that is not cultured prior to the extraction of nucleic acids from the sample.

In some embodiments, the *Tritrichomonas* spp. gene or *Trichomonas* spp. gene is a ribosomal RNA (rRNA) gene, such as the 5.8 S rRNA gene. For methods and kits testing for a *Tritrichomonas* spp. gene, the primer set can comprise a forward primer comprising the nucleotide sequence of 5'-GCGGCTGGATTAGCTTTCTTT-3' (SEQ ID NO:1) and a reverse primer comprising the nucleotide sequence of 5'-GGCGCGCAATGTGCAT-3' (SEQ ID NO:2), or, alternatively, the primer set can comprise a forward primer comprising the nucleotide sequence of 5'-GAACGTTG-CATAATGCGATAAGC-3' (SEQ ID NO:3) and a reverse primer comprising the nucleotide sequence of 5'-AACATATATGCGTGTTCTAGCAAGCT-3' (SEQ ID NO:4). In some embodiments, the primer set comprises a forward primer comprising a nucleotide sequence selected from the group consisting of SEQ ID NO:1 and SEQ ID NO:3 and a reverse primer comprising a nucleotide sequence selected from the group consisting of SEQ ID NO:2 and SEQ ID NO:4.

In additional embodiments, the qPCR or RT-qPCR method detection of the PCR amplicon step further comprises hybridizing a probe comprising the nucleotide sequence of 5'-ACAAGTTCGATCTTTG-3' (SEQ ID NO:5) or 5'-ATCTTTGAATGCACATTGCGCGCC-3' (SEQ ID NO:6). Markers, such as dyes, radioisotopes, fluorescent labels and the like, may be incorporated or linked to the nucleotide sequence of the hybridizing probe to provide for a detectable signal to aid in analysis, such as for analyzing the qPCR product amplification in real-time.

Thus, the following non-limiting embodiments are provided:

1. A quantitative polymerase chain reaction (PCR) method for diagnosing trichomoniasis in a subject sample, the method comprising:
   receiving the sample;
   extracting nucleic acids from the sample and said sample is, optionally, not cultured prior to the extraction of said nucleic acids;
   carrying out a qPCR on the nucleic acids with a primer set comprising a forward primer and a reverse primer, wherein the primer set permits the generation of a PCR amplicon that includes a region of a *Tritrichomonas* spp. gene or a *Trichomonas* spp. gene; and
   detecting the PCR amplicon;
   wherein the presence of the PCR amplicon indicates a positive diagnosis of trichomoniasis.

2. The quantitative PCR method according to embodiment 1 wherein the sample is a smegma sample and wherein said sample is, optionally, not cultured prior to the extraction of nucleic acids from said sample.

3. The quantitative PCR method according to embodiment 2 wherein the sample is a bovine, human, canine or feline smegma or cervical/uterine fluid sample.

4. The quantitative PCR method according to embodiments 1-3 wherein the *Tritrichomonas* spp. gene or *Trichomonas* spp. gene is a ribosomal RNA (rRNA) gene.

5. The quantitative PCR method according to embodiment 4 wherein the rRNA gene is a 5.8 S rRNA gene.

6. The quantitative PCR method according to embodiments 1-5 wherein the primer set comprises a forward primer comprising the nucleotide sequence of SEQ ID NO:1 and a reverse primer comprising the nucleotide sequence of SEQ ID NO:2.

7. The quantitative PCR method according to embodiments 1-5 wherein the primer set comprises a forward primer comprising the nucleotide sequence of SEQ ID NO:3 and a reverse primer comprising the nucleotide sequence of SEQ ID NO:4.

8. The quantitative PCR method according to embodiments 1-5 wherein the primer set comprises a forward primer comprising a nucleotide sequence selected from the group consisting of SEQ ID NO:1 and SEQ ID NO:3 and a reverse primer comprising a nucleotide sequence selected from the group consisting of SEQ ID NO:2 and SEQ ID NO:4.

9. The quantitative PCR method according to embodiments 1-6 wherein the step of detecting the PCR amplicon comprises the step of hybridizing a probe comprising the nucleotide sequence of SEQ ID NO:5.

10. The quantitative PCR method according to embodiments 1-7 wherein the step of detecting the PCR amplicon comprises the step of hybridizing a probe comprising the nucleotide sequence of SEQ ID NO:6.

11. The quantitative PCR method according to embodiments 1-7 wherein the step of detecting the PCR amplicon comprises the step of hybridizing a probe comprising the nucleotide sequence of SEQ ID NO:5.

12. The quantitative PCR method according to embodiment 8 wherein the step of detecting the PCR amplicon comprises the step of hybridizing a probe comprising the nucleotide sequence of SEQ ID NO:5.

13. A kit for the detection of *Tritrichomonas* spp. or *Trichomonas* spp., the kit comprising:
   a primer set comprising a forward primer and a reverse primer, wherein the forward primer and the reverse primer are capable of generating a PCR amplicon from a region of one or more *Tritrichomonas* spp. gene or *Trichomonas* spp. gene; and
   a probe capable of hybridizing to the PCR amplicon.

14. The kit according to embodiment 13 further comprising an exogenous internal positive control polynucleotide and the respective internal positive control primer set comprising a control forward primer and a control reverse primer wherein the control forward primer and the control reverse primer are capable of generating a control PCR amplicon from the exogenous internal positive control polynucleotide.

15. The kit according to embodiment 14 wherein the exogenous internal positive control polynucleotide comprises the nucleotide sequence of SEQ ID NO:8.

16. The kit according to embodiments 14-15 wherein the control forward primer comprises the nucleotide sequence of SEQ ID NO:9 and wherein the control reverse primer comprises the nucleotide sequence of SEQ ID NO:10.

17. The method according to embodiments 1-12, wherein the sample is not cultured prior to the extraction of said nucleic acids.

18. The method according to any preceding embodiment, wherein the qPCR method is a RT qPCR method.

MATERIALS AND METHODS

The following materials, methods, and protocols were used for the methods and kits exemplified herein. The following protocol provides procedures for sample collection and nucleic acid purification and amplification for the detection of *Tritrichomonas foetus* (*T. foetus*). *T. foetus* causes disease in bovine and feline and the methods described below are applicable for *T. foetus* detection in all species. In bovine, *T. foetus* causes trichomoniasis which is characterized by infertility, early embryonic death, rare abortions and pyometra in cows and heifers. Samples required for diagnostic testing include cervical mucus/uterine fluids from cows, and scrapings of the prepuce (smegma) from bulls. In feline, *T. foetus* causes diarrhea, and feces is required for diagnosis. Bovine specific methods are described below, however the core technology of *T. foetus* nucleic acid amplification is also applicable for detection of *T. foetus* in feline and other animals. The protocol below is divided into three sections: sample collection, nucleic acid purification, and nucleic acid amplification. The advantage of the methods described below is that biological sample is used directly for nucleic acid purification, without the need for pre-culture, therefore reducing time and money while enabling faster diagnosis.

Sample Collection

Bull Smegma Sample Collection

The rear leg is "dallied" with cotton rope to reduce risk of injury to the collector. Next, the prepuce is ensured to be clean and washed with 10 mL of saline (or equivalent) before collection, avoiding fecal and dirt contamination. Using a sterile mare inseminating pipette scrape attached with a 12 cc syringe, suction (negative pressure) is applied and the prepuce scraped 10 times. Smegma is placed into a 2-4 mL (or equivalent) tube containing 1000 µL of pre-filled 1×PBS (~pH 7.4) or Saline (0.9% NaCl or equivalent); up to 2000 µL liquid may be pre-filled if 4 mL tube is used. The smegma is then pipetted up and down to release into the tube. Next, the smegma sample is placed into a small sample storage box and the box placed into the bottom of a Styrofoam box and an ice pack placed on top of the sample box for sample shipment or transfer to the diagnostic laboratory. Samples should be stored in the fridge (~4° C. or equivalent), not frozen until ready for further processing. Post-testing/analysis, samples should be store frozen (~−20° C. or equivalent) for sample archiving or long term storage in desired.

Cow Sample Collection

The vulvar area is ensured to be clean and washed with 10 mL of saline (0.9% NaCl or equivalent), avoiding fecal and dirt contamination. Using a sterile mare inseminating pipette scrape attached with a 12 cc syringe, suction (negative pressure) is applied and cervical mucous/uterine fluid aspirated. The cervical mucus, or uterine fluids, is placed into 2-4 mL (or equivalent) tubes filled with 1000 µl 1×PBS (~pH 7.4) or Saline (0.9% NaCl or equivalent) and pipetted up and down to release the sample into the tube; up to 2000 µL liquid may be pre-filled if 4 mL tube is used. Next, the sample is placed into a small sample storage box and the box placed into the bottom of a Styrofoam box and an ice pack placed on top of the sample box for sample shipment or transfer to the diagnostic laboratory. Samples should be stored cold, not frozen until ready for further processing.

Nucleic Acid Purification

Note: Alternative nucleic acid methods using magnetic beads or silica filter columns are applicable.

Equipment, Supplies, and Reagents
1. Vortexer, any vendor
2. Kingfisher 96/MagMAX Express-96/BioSprint 96
3. 8×12 array tube rack (i.e, VWR, Part Number 60986-158 or equivalent)
4. 25-50 mL Reagent Reservoir, any vendor
5. Multi-channel pipettes, single pipettes, and filtered pipette tips (any vendor)
6. Plate sealers (Phenix Research, Part Number LMT-SEAL-EX or equivalent)
7. Large bore filtered tips or cut filtered tips for pipetting viscous smegma samples
8. Barnsted/Lab-line Plate Shaker (VWR cat #57019-600) or equivalent
9. MagMAX-96 Viral RNA Isolation Kit (Life Technologies, Part Number AMB1836-5, or larger kit size)
10. MagMAX™ Lysis/Binding Solution Concentrate (Life Technologies, Part Number AM8500, 100 mL)
11. XIPC RNA (10,000 copies/µl, optional)
12. ~100% Ethanol
13. ~100% Isopropanol
14. MagMAX™ Express-96 Deep Well Tip Combs (Life Technologies, Part Number 4388487 or equivalent)
15. MagMAX™ Express-96 Deep well Plates (Life Technologies, Part Number 4388476 or equivalent)
16. MagMAX™ Express-96 Standard Plates (Life Technologies, Part Number 4388475 or equivalent)

Reagent Preparation

Lysis/Binding Solution Concentrate

The entire contents of a MagMAX-96 Viral RNA Isolation Kit (Life Technologies, Part Number AMB1836-5) is added to 100 mL MagMAX™ Lysis/Binding Solution Concentrate (Cat # AM8500) and mixed well. The solution concentrate is stored at room temperature until use. Note: DO NOT add isopropanol to the Lysis/Binding Solution Concentrate.

Lysis Solution

For one reaction, the following is added in order:
i. 200 µL Lysis/Binding Solution Concentrate
ii. 1 µL Carrier RNA (1 µg/µL)
iii. 1 µL XIPC RNA (10,000 copies/µL)
iv. 200 µL ~100% Isopropanol
v. Mix well by vortexing and store at room temperature.

Bead Mix 20 mL of Bead Mix is used for each reaction. For one reaction, the following is combined in order:
i. 10 µL of RNA Binding Beads; shake beads well before aliquotting.
ii. 10 µL of Lysis/Binding Enhancer.
iii. Mix well by vortexing; store on ice.

Wash Solution 1 and Wash Solution 2

Prepare as directed by manufacturer and mix well and store at room temperature.

Nucleic Acid Purification

The plates are prepared as described below. For best results, the sample plate is prepared last to reduce the time that sample, Bead Mix, and isopropanol are unmixed and immediately load the plate onto the magnetic particle processor. MagMAX™ Express-96 Deep Well Tip Combs (Life Technologies, Part Number 4388487) are utilized. Tip Combs are examined to ensure that no defects/holes are visible; one Deep Well Tip Comb is loaded into one standard well plate (MagMAX™ Express-96 Standard Plates (Life Technologies, Part Number 4388475 or equivalent). 90 µL of Elution Buffer is loaded into one standard well plate. 300 µL Wash Solution 2 is loaded into one deep well plate, and 300 µl Wash Solution 1 is loaded into another deep well plate. The loaded plates are stacked on top of each other and the top plate covered to avoid reagent evaporation and debris.

A sample plate (deep well plate) is prepared. 20 µL Bead Mix is added and followed by ~50 µL of the biological sample using a p1000 pipette tip due to high viscosity of the samples. Additionally, the longer p1000 pipette tip enables sample transfer from the collection tube without complete submersion of the tip into the collection tube thus reducing the chance of cross-contamination. The plate is shaken at moderate setting (#7-8) for 2-5 minutes. Note: ensure that Bead mix is deposited at the bottom of the sample well and sample is deposited into the bead mix; sample should contact bead mix which contains enzymes that will aid in sample lysis. 400 μL Lysis Binding Solution (LBS) is added into each sample well.

The "AM1836 DW One" magnetic bead processor heated elution protocol (as described in Schroeder et al 2013) is selected on a magnetic particle processor. The plates are loaded according to the Reagents Plate Table (Table 1) for nucleic acid purification. Upon completion of the nucleic acid purification, the elution plate is removed and stored on ice for immediate usage (the elution is hot; thus, ice storage prevents the probability of reverse transcriptase inactivation during RT-qPCR). For long-term storage, the plate is sealed with a plate sealer and stored frozen at ~−20-80° C.

TABLE 1

| Protocol/Program Name | AM1836 DW One | | |
|---|---|---|---|
| Magnetic Head | Deep Well Magnetic Head, AB# 4388435 | | |
| Tip Comb | Deep Well Tip Combs, AB# 4388487 | | |
| Sample Volume (μl) | 50-270 μl (see individual protocol) | | |
| Plate #/Position, Name | Reagents and Usage (μl) | | Plate |
| 1   Lysis Binding | Load reagents in the listed | | Deep |
| | Bead Mix | 20 μl | Well |
| | Sample | 50 μl | Plates |
| | Shake at #7-8 for at least 2 min | | |
| | Remove plate from shaker | | |
| | Add following & place on KF-96 | | |
| | Lysis Binding Soln | 400 μl | |
| 2   Wash 1 | Wash Solution 1 | 300 μl | |
| 3   Wash 2 | Wash Solution 2 | 300 μl | |
| 4   Elution | Elution Buffer | 90 μl | Standard |
| 5   Tip Comb Plate | Deep Well Tip Comb | | Plates |

Nucleic Acid Amplification
Equipment, Supplies, and Reagents
1. Vortexer, any vendor
2. NanoDrop Spectrophotometer or equivalent
3. Multi-channel pipettes, single pipettes, and filtered pipette tips
4. 7500/7500 Fast Real-Time PCR Systems or equivalent
5. Eppendorf MixMate or equivalent
6. Mini Plate Spinner/Centrifuge or equivalent
7. 96-well cold block, any vendor
8. Fast Optical 96 well Plate (Life Technologies, Part Number 4346907)
9. MicroAmp Optical Adhesive Film (Life Technologies, Part Number 4311971)
10. TE (0.1) pH 8.0 (10 mM Tris, 0.1 mM EDTA), IDTE (Integrated DNA Technologies or equivalent)
11. Primers, preferred vendor is Biosearch Technologies; reverse-phase cartridge purification
12. Black hole quencher probes, preferred vendor is Biosearch Technologies; HPLC purification
13. Minor groove binder probes, Life Technologies; HPLC purification
14. Carrier RNA (1 mg/ml, Life Technologies, Part Number 4382878)
15. Path-ID™ qPCR Master Mix (Life Technologies, Part Number 4388644 or equivalent)
16. ArrayScript™ Reverse Transcriptase (Life Technologies, Part Number AM2049 or equivalent)

*T. foetus* Nucleic Acid Amplification

Two *T. foetus* amplification assays targeting the 5.8s rRNA are provided herein, termed the McMillen assay and the TVMDL assay. Both assays perform equivalently based on diagnostic specificity and sensitivity evaluation.

Primer Probe Mix (25×) Preparation

Verify oligo concentration using a spectrophotometric method (i.e. NanoDrop or equivalent). Refer to the "TaqMan RNA-to-Ct 1-Step Kit" manual, Part Number 4393463 Rev. C for reference, and adjust the calculations for cuvette path length appropriately based on spectrophotometer used. Next, prepare each lot of 25× Primer Probe Mix (PPM) as needed. Use the "25×" μM in Table 2 as the required/final oligo concentration in the 25× PPM to determine the required amount of stock oligos based on concentration of stock oligos. Mix the required volume of stock oligos and IDTE (suspension liquid) well by vortexing at moderate setting for at least 5 seconds. Then, aliquot ~120 μl of 25×PPM into appropriately labeled 1.5 ml amber tubes and store at ~−20° C.

TABLE 2

| Name | Sequence; 5' > 3' | Dye-Quencher | 1X conc [nM] | 25X conc [μM] |
|---|---|---|---|---|
| *T. foetus* (McMillen)-XIPC Primer Probe Mix | | | | |
| T.foeF | GCGGCTGGATTAGCTTTCTTT (SEQ ID NO: 1) | none | 500 | 12.5 |
| T.foeR | GGCGCGCAATGTGCAT (SEQ ID NO: 2) | none | 500 | 12.5 |
| T.foepb | ACAAGTTCGATCTTTG (SEQ ID NO: 5) | FAM/MGB | 125 | 3.1 |
| XIPCF695 | TTCGGCGTGTTATGCTAACTTC (SEQ ID NO: 9) | none | 250 | 6.3 |
| XIPCR764 | CCACTGCGCCCAACCTT (SEQ ID NO: 10) | none | 250 | 6.3 |
| XIPC_pb722 | CTCCGCAGAAATCCAGGGTCATCG (SEQ ID NO: 11) | CFO560/BHQ1 | 60 | 1.5 |
| *T. foetus* (TVMDL)-XIPC Primer Probe Mix | | | | |
| T.foeF2 | GAACGTTGCATAATGCGATAAGC (SEQ ID NO: 3) | none | 450 | 11.3 |
| T.foeR1 | AACATATATGCGTGTTCTAGCAAGCT (SEQ ID NO: 4) | none | 450 | 11.3 |
| T.foepb1 | ATCTTTGAATGCACATTGCGCGCC (SEQ ID NO: 6) | FAM/BHQ1 | 125 | 3.1 |
| XIPCF695 | TTCGGCGTGTTATGCTAACTTC (SEQ ID NO: 9) | none | 200 | 5.0 |
| XIPCR764 | CCACTGCGCCCAACCTT (SEQ ID NO: 10) | none | 200 | 5.0 |

TABLE 2-continued

| Name | Sequence; 5' > 3' | Dye-Quencher | 1X conc [nM] | 25X conc [µM] |
|---|---|---|---|---|
| XIPC_pb722 | CTCCGCAGAAATCCAGGGTCATCG (SEQ ID NO: 11) | CF0560/BHQ1 | 125 | 3.1 |

Note:
"FAM" = 6-carboxyfluorescein; "MGB" = minor groove binder; "BHQ1" = black hole quencher 1

Control RNA Preparation

Two control RNA transcripts are utilized in the *T. foetus* detection workflow. A universal exogenous internal positive control (XIPC) RNA which contains noninfectious unique artificial antigenomic sequence (GenBank Accession DQ883679) and possesses no significant homology to the current annotated public sequences data, can serve as a universal internal positive control for diverse quantitative PCR assays. The XIPC ensures that a true negative result is due to lack of target nucleic acid as opposed to a false negative result due to the absence of target (due to a non-functional nucleic acid purification process) or presence of PCR inhibitors. The XIPC RNA can be used for both nucleic acid purification and amplification internal controls. The use of XIPC has been reported in (Schroeder et al., *JVDI*, 2013; Wilson et al., *J. Virol. Med.*, 2013; and Schroeder et al., *JVDI*, 2012). The XIPC RNA control sequence is provided by SEQ ID NO:7, and the corresponding DNA sequence is provided by SEQ ID NO:8. The forward XIPC primer (XIPCF695) comprises the nucleotide sequence of SEQ ID NO:9, and the reverse XIPC primer (XIPCR764) comprises the nucleotide sequence of SEQ ID NO:10. The probe utilized for hybridization to XIPC (XIPC_pb722) comprises the nucleotide sequence of SEQ ID NO:11.

The *T. foetus* control RNA contains the *T. foetus* RT-qPCR assays target sequences. This control RNA serves as the positive amplification control during each RT-qPCR run to ensure functionality of RT-qPCR reagents and instrument and also utilized to set the threshold cycle (Ct) for evaluation of test samples. The RNA sequence for these controls is provided in SEQ ID NO:12, and the corresponding DNA sequence is provided in SEQ ID NO:13.

The independent DNA plasmids containing the XIPC and *T. foetus* RNA are utilized for in vitro transcription using standard manufacturer's protocols. Any vendor's in vitro transcription reagents may be utilized.

The vectors utilized include:
*T. foetus* control: Vector; pBluescript II SK+ (Stratagene cat #212205), 2961 bp; use T7 promoter: GGGCGAATTGGG-TAC (SEQ ID NO:14); Vector DNA sequence Sequence info: *T. foetus* (AF466751, nt 1461-1895); 435 nt *T. foetus* cloned into Kpn I/HindIII site.
XIPC control: Vector; pBluescript II SK+ (Stratagene cat #212205), 2961 bp; use T7 promoter: GGGCGAATTGGG-TAC (SEQ ID NO:14); Vector DNA sequence Sequence info: Synthetic construct clone NISTag38 (DQ883679.2, 1000 nt); cloned into Kpn I/HindIII site.
T7 Terminator sequence:

(SEQ ID NO: 15)
TGAAACTAGCATAACCCCTTGGGGCCTCTAAACGGGTCTTGAGGGGTTT

TTTGA.

In vitro transcribed RNAs are analyzed to verify correct size using electrophoresis and the concentration determined using absorbance 280 analysis. Copy numbers are determined using the following formula:

$$\text{Number of } RNA \text{ copies per 1 ng} = \frac{1 \text{ ng} * 6.02 \times 10^{23} \text{ copies/mole}}{RNA \text{ transcript molecular weight (g/mole)} * 1 \times 10^9 \text{ ng/g}}$$

Next, a nucleic acid dilution solution (NADS) is prepared by diluting carrier RNA 1 mg/mL to 10 ng/µL using IDTE as the diluent. Prepare the appropriate volume as needed and mix well by vortexing at least 5-10 seconds. Store cold for short term usage and frozen for long term usage.

Next, dilute the XIPC RNA transcript to 10,000 copies/µL using NADS. This is required for spiking into the lysis solution during the nucleic acid purification process. Then, dilute the *T. foetus* RNA and XIPC RNA to 1,000 copies/µL each in the same tube using NADS to make the positive amplification control (PAC) mix.

Reverse Transcription-Quantitative Real-Time PCR (RT-qPCR)

Prepare PCR system "Document" as follows. If an alternative system is used, change the instrument type, software, and plate/tubes appropriately.

i. Instrument Type: AB 7500 Fast RTPS: Assay: Standard Curve (Absolute Quantification)

ii. Container: 96-Well Clear: Template: Blank Template iii. Run Mode: Standard: Software: SDS v1.4 or equivalent iv. *T. foetus*=FAM; XIPC=CF0560: Quencher: none for all detectors v. Passive Reference: ROX Next, prepare the PCR system "Instrument" Tab as follows:

| Stage | Reps | Temp | Time |
|---|---|---|---|
| 1 | 1 | 48.0° C. | 10 min |
| 2 | 1 | 95.0° C. | 10 min |
| 2 | 40 | 95.0° C. | 15 sec |
|  |  | 55.0° C. | 45 sec | vi. Sample volume=25 µL; Run Mode=Standard; Data Collection=Stage 2 Step 2

Prepare the RT-qPCR mastermix using PCR components below. Determine the required volume for desired reaction using the single reaction required volume below.

For one reaction (25 µL), combine:

| | |
|---|---|
| 12.5 µL | 2X Path-ID qPCR Buffer |
| 0.05 µL | Arrayscript (200 units/µl) |
| 1.0 µL | 25X PPM |
| 6.2 µL | Nuclease-free water |
| 20.0 µL | Total Volume |

Distribute 20 µL of the mastermix into each well of a PCR plate; for best practice, place plate on cold block.

Add 5 µL of each sample (purified NA, PAC, and H$_2$O) below to each well, seal, mix, pulse spin, and place reactions into PCR system. The Eppendorf MixMate and Mini plate spinner are recommended for plate mixing and pulse spinning.

Perform data analysis using Auto Baseline and Manual Ct.

Figure 6:
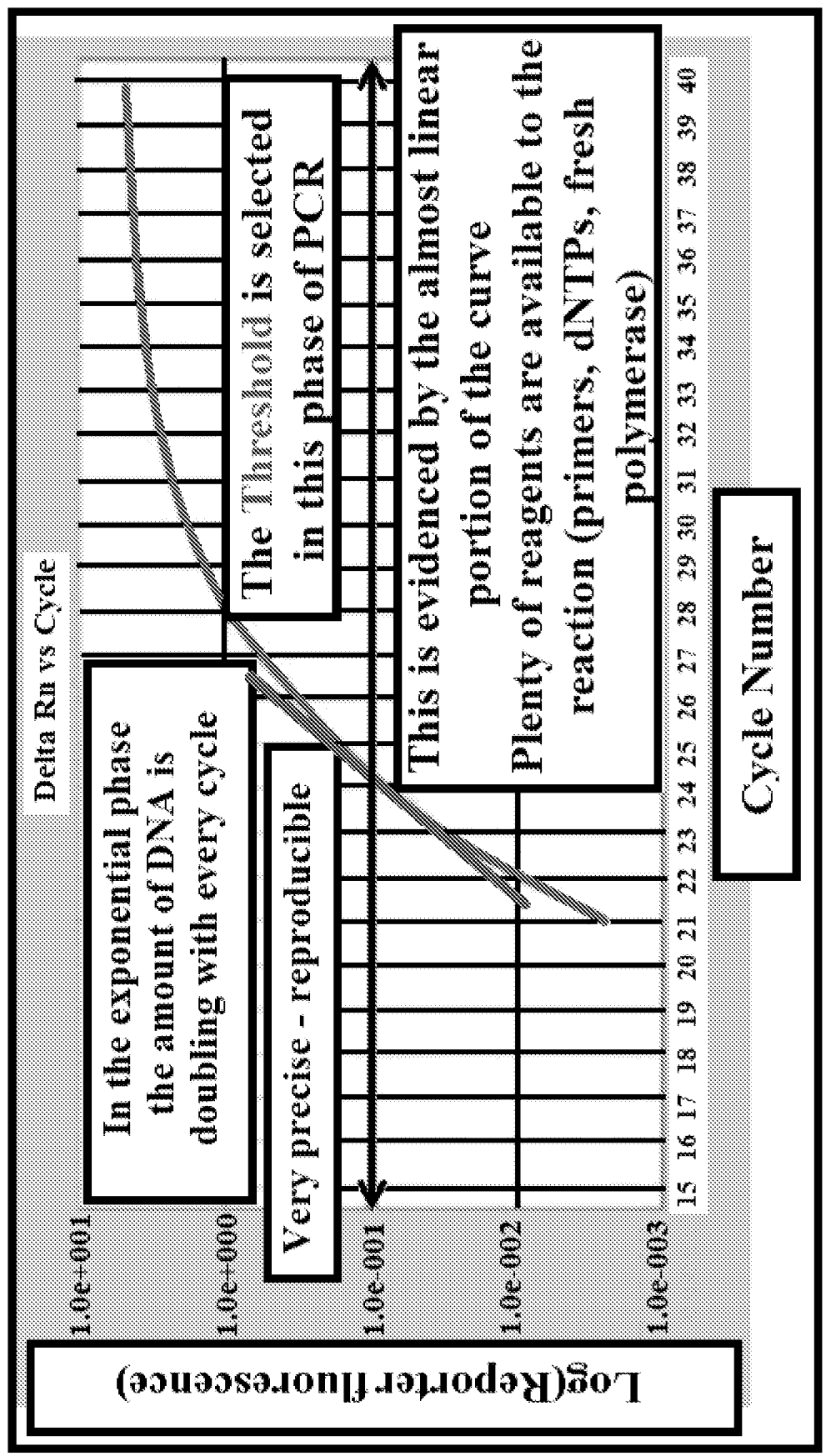
FIG. 6 shows a graph of fluorescence values by cycle number during a qPCR reaction of an embodiment of the present invention. Linear dynamic range and efficiency of the Direct Sample RT-qPCR workflow.

Set the threshold for target reactions at 5-10% of the maximum fluorescence value (dRn Max) of the PAC amplification signal in control reactions; adjust threshold (percent) appropriately to ensure that it is set at the exponential phase of the amplification curve (see FIG. 6). Recommended settings are: 10% dRn Max for *T. foetus* (McMillen)-XIPC assay for both *T. foetus* and XIPC amplifications and 5% dRn Max for *T. foetus* (TVMDL)-XIPC assay for both *T. foetus* and XIPC amplifications.

Review the amplification curves to ensure lack of deviant amplification curves. If deviant curves are observed, adjust the manual baseline appropriately based on the amplification signal for all reactions and set Ct appropriately.

For positive reactions, deviant curves, or late amplification reactions, check the raw fluorescence data in the "Component" view and verify that fluorescence increases seen in the normalized data are also evident without mathematical data processing.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All percentages are by weight and all solvent mixture proportions are by volume unless otherwise noted.

Example 1—Validation of Nucleic Acid Detection Method for *T. foetus*

Historical testing methods for *T. foetus* include a culture test that requires daily microscopic examination for up to six days or nucleic acid detection of cultured samples by PCR. For both methods, smegma samples are collected into a culture media pouch (InPouch containing ~3.7 mL, approx. $5/pouch) and incubated at ~37 degrees Celsius for at least 48 hours (PCR) and up to 6 days (microscopic examination). For PCR, ~300 uL of InPouch sample is used for nucleic acid purification and *T. foetus* DNA (5.8 S ribosomal RNA (rRNA) gene) detection.

For the initial feasibility testing of the current invention, the TVMDL currently employed *T. foetus* qPCR (denoted as Culture below) were used to identify *T. foetus* positives. The respective smegma samples were also tested with the method provided by the current invention (denoted as Direct Sample in Table 3). The PCR cycle threshold (Cq) were compared, ΔCq denotes the "Direct Cq-Culture Ct". The results indicate that the invention method enables identification of all positives (100% sensitivity) and better sensitivity as evidenced by earlier Cq (3.3 Cq difference is equivalent to 10 fold difference in target copy numbers). In addition to these positive samples, 609 samples which were from *T. foetus* low risk herds and previously identified as negative by the Culture qPCR were also evaluated for specificity and all samples were negative by the Direct Sample RT-qPCR.

TABLE 3

| Positive Bull ID | Culture Cq | Direct sample Cq | ΔCq (DS-C) |
|---|---|---|---|
| House Call | 29.1 | 19.1 | −10.0 |
| Cat Daddy | 35.0 | 23.4 | −11.6 |
| H1 | 27.2 | 20.1 | −7.1 |
| H2 | 27.9 | 22.2 | −5.6 |
| H18 | 31.8 | 26.0 | −5.8 |
| H19 | 34.4 | 28.6 | −5.8 |
| H25 | 27.4 | 20.3 | −7.1 |
| H26 | 32.6 | 24.2 | −8.4 |
| 234 Baker | 25.2 | 18.3 | −6.9 |
| K17 | 33.7 | 29.2 | −4.5 |
| K99 | 24.2 | 24.5 | 0.3 |
| K46 | 34.8 | 29.7 | −5.1 |

The linear dynamic range, efficiency, and relative analytical sensitivity of the workflow consisting of nucleic acid purification and RT-qPCR was assessed by using spiked serially diluted *T. foetus* organisms (estimated by cell counting) into smegma samples and linear regression analysis. Relative analytical sensitivity in this content refers to the minimum amount of *T. foetus* nucleic acid that can be detected based on a *T. foetus* organism serial dilution input and not on organisms per reaction since cell counting is inherently inaccurate. The workflow exhibited a 108% efficiency (95% CI, 103.5% to 112.5%) and R2 of 0.989, for a ten-fold dilution series that spanned a 5 log dynamic range with 12 replicates for each *T. foetus* organism input dilution (FIG. 1, McMillen assay). The average XIPC Cq value for all RT-qPCR performed by both operators was 30.4±0.07 and CV was 0.24% (FIG. 1, McMillen assay); the performance of the TVMDL assay was equivalent and also provided in FIG. 1.

Figure 2:
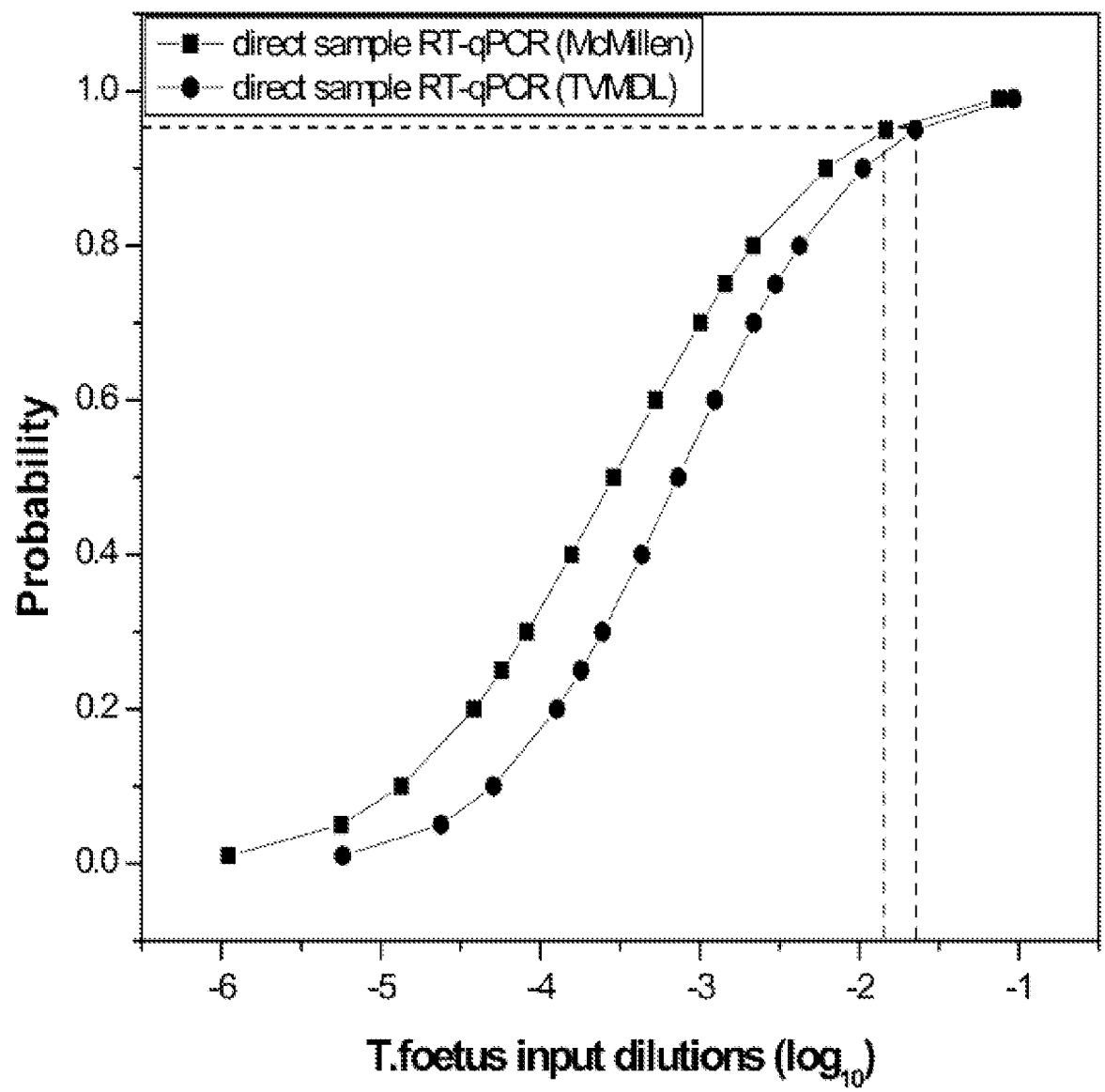
FIG. 2. Probit analysis of *T. foetus* organism detection by the Direct Sample RT-qPCR workflow. Two-fold dilutions of *T. foetus* were prepared in negative bovine smegma and used for nucleic acid purification and detection. A total of eight responses for each input dilution were analyzed in order to determine the dilution corresponding to a detection rate of 95% and the limit of detection at 95% was determined from this analysis. Results for McMillen and TVMDL assays/oligos are provided.

Relative analytical sensitivity of the workflow was assessed by Probit analysis. A total of eight results/responses for each of nine two-fold organism input/dilutions were used to determine the 95% RT-qPCR detection rate; Cq values below 40 were considered a positive response or amplification for this analysis. RNA copy number equivalents for the 95% detection rate were estimated using a separate set of RT-qPCR targeting serial dilutions of an in vitro transcribed *T. foetus* control RNA and linear regression analysis. Probit analysis indicated that the limit of detection for the *T. foetus* RT-qPCR workflow is ~30 target copies (~36.3 $C_q$) per RT-qPCR using McMillen assay, and ~50 target copies (~35 $C_q$) using TVMDL assay. The Probit plot is shown in FIG. 2 for McMillen and TVMDL assays.

Figure 3:
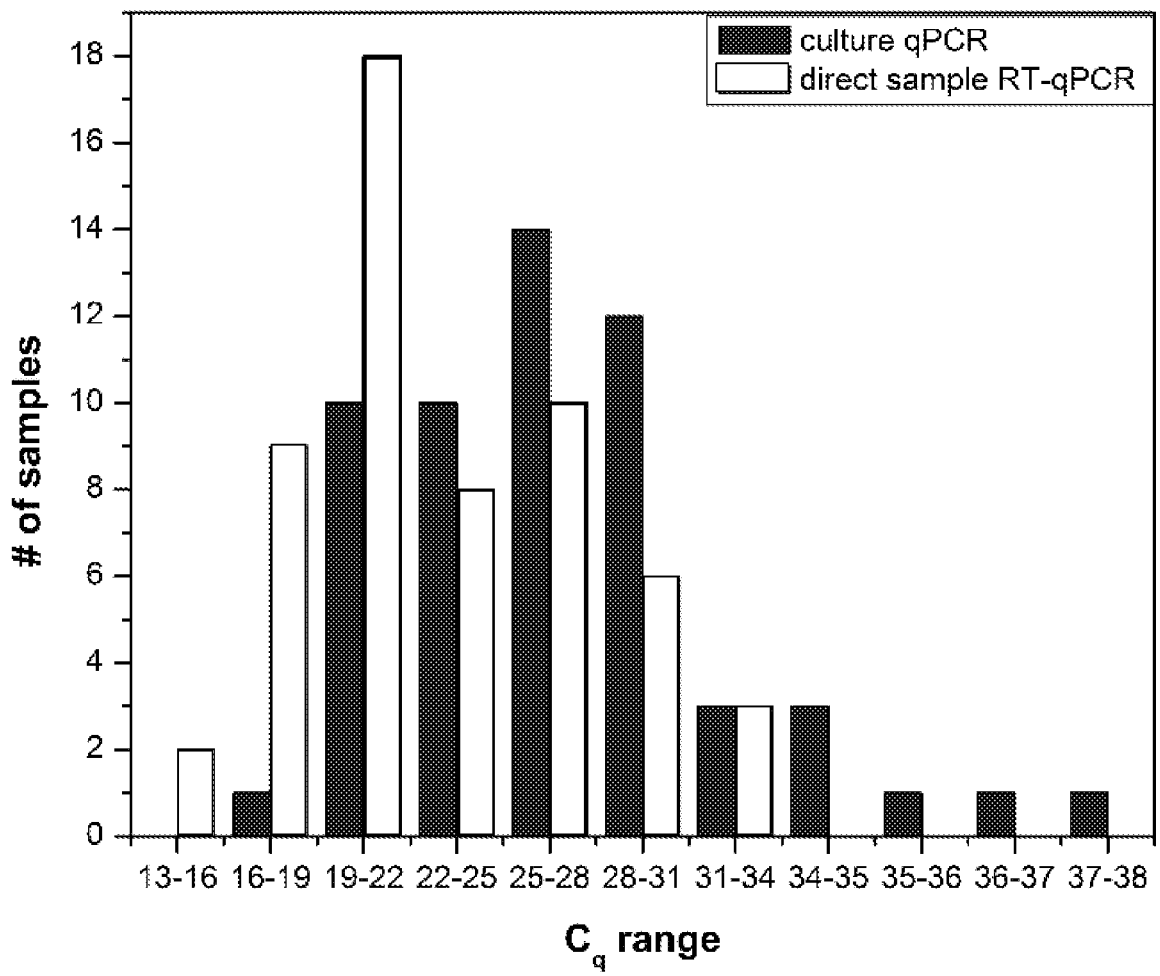
FIG. 3. Direct Sample RT-qPCR and Culture qPCR $C_q$ values frequency distributions for 56 Culture Readings positives. Cq value frequency distributions in samples from 56 *T. foetus* culture positive bulls utilizing the direct sample RT-qPCR of the present invention versus the traditional method (Culture qPCR).
Figure 4:
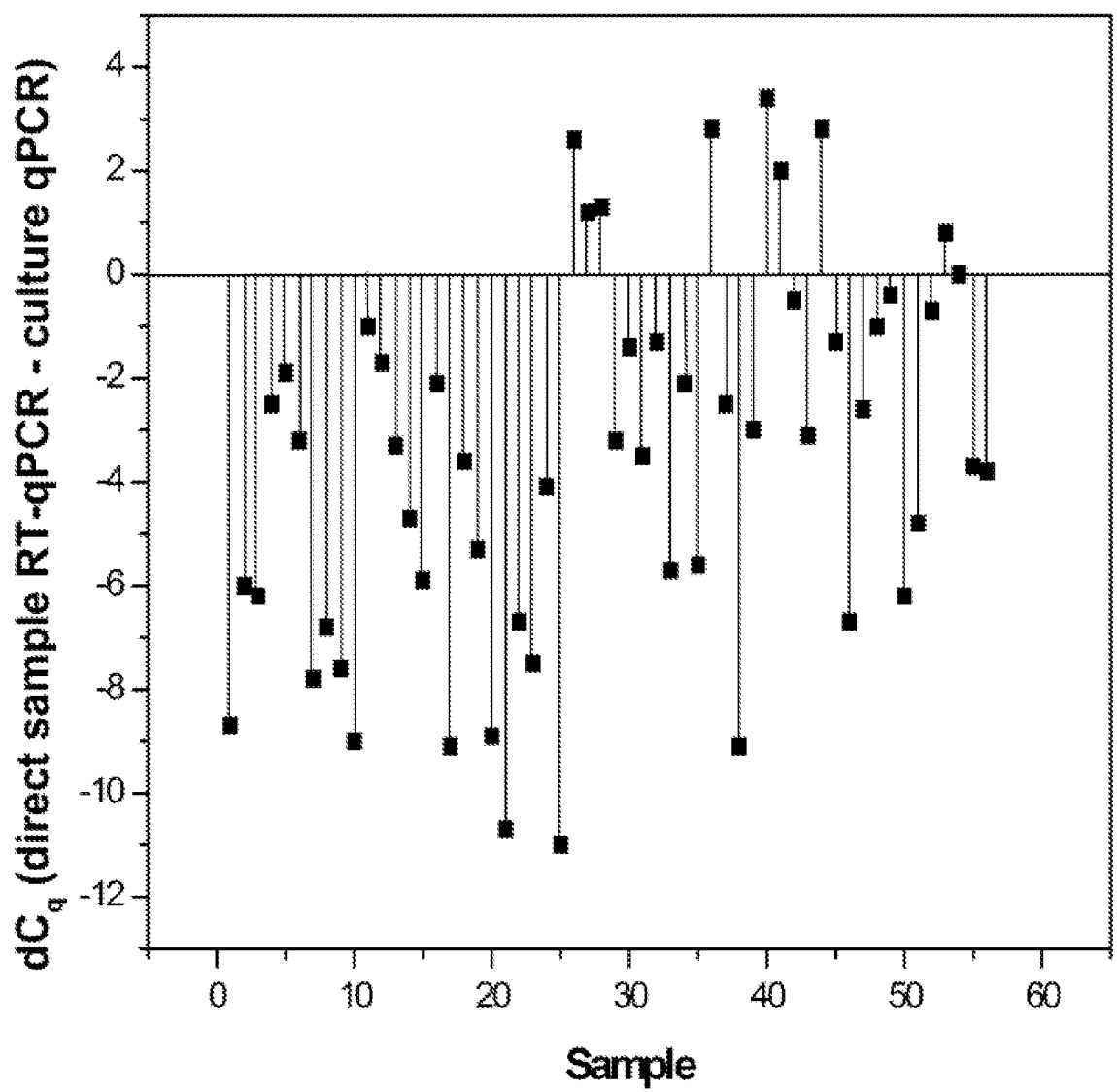
FIG. 4. Direct Sample RT-qPCR and Culture qPCR $C_q$ values difference plot for 56 Culture Reading positives. The y-axis represents the difference in $C_q$ value between the two workflows; negative values indicates that the Direct Sample RT-qPCR results in lower $C_q$ values, indicating enhanced detection sensitivity.

Diagnostic performance of the Direct Sample RT-qPCR was evaluated using a total of 166 bulls, 56 positives and 110 negatives. *T. foetus* positive or negative status was determined using the InPouch culture microscopic examination. Using microscopic examination as the reference test, the Culture qPCR, which utilizes cultured samples in InPouch media, exhibited 95% diagnostic sensitivity and 100% specificity and McNemar's P-value was 0.25. The Direct Sample RT-qPCR (both McMillen and TVMDL assays) of the present invention exhibited 100% diagnostic sensitivity and 99% specificity; agreement between the Direct Sample RT-qPCR and microscopic examination was 99% (kappa=0.99); McNemar's P-value was 1.00; no significant difference was observed between the RT-qPCR and the microscopic examination. The positive samples average XIPC Cq was 32.6±1.1; negative samples average XIPC Cq was 32.2±1.5; these results indicate proper functionality of nucleic acid purification and detection methods. Specificity of the Direct Sample RT-qPCR was also assessed using 543 samples collected from low-risk herds with good reproductive history and have been previously tested negative by the Culture qPCR; these samples were found to be negative by the Direct Sample RT-qPCR and the concurrent Culture qPCR testing. In the diagnostic performance evaluation using 166 reference bulls, the agreement between the Culture qPCR and the Direct Sample RT-qPCR was 98% (kappa=0.95) and P-value was 0.125, indicating no significant difference between the two tests. However, the Direct Sample RT-qPCR identified four additional positive animals and $C_q$ values were significantly lower for positives: 13.6-33.5 for Direct Sample RT-qPCR vs. 18.7-37.4 for Culture qPCR ($p<0.05$; FIG. 3). The average Cq value for the Direct Sample RT-qPCR was 22.9±4.5, while the average Cq value for the Culture qPCR was 26.5±4.6, and a paired t-test indicated significant difference (p=0.0007). The difference between Cq values (Direct Sample RT-qPCR-Culture qPCR) ranged from (−)11.0 to (+) 3.4 (FIG. 4). The lower $C_q$ range of the Direct Sample RT-qPCR results enabled better data interpretation since all $C_q$ values were outside of the inconclusive and suspect range.

Figure 5:
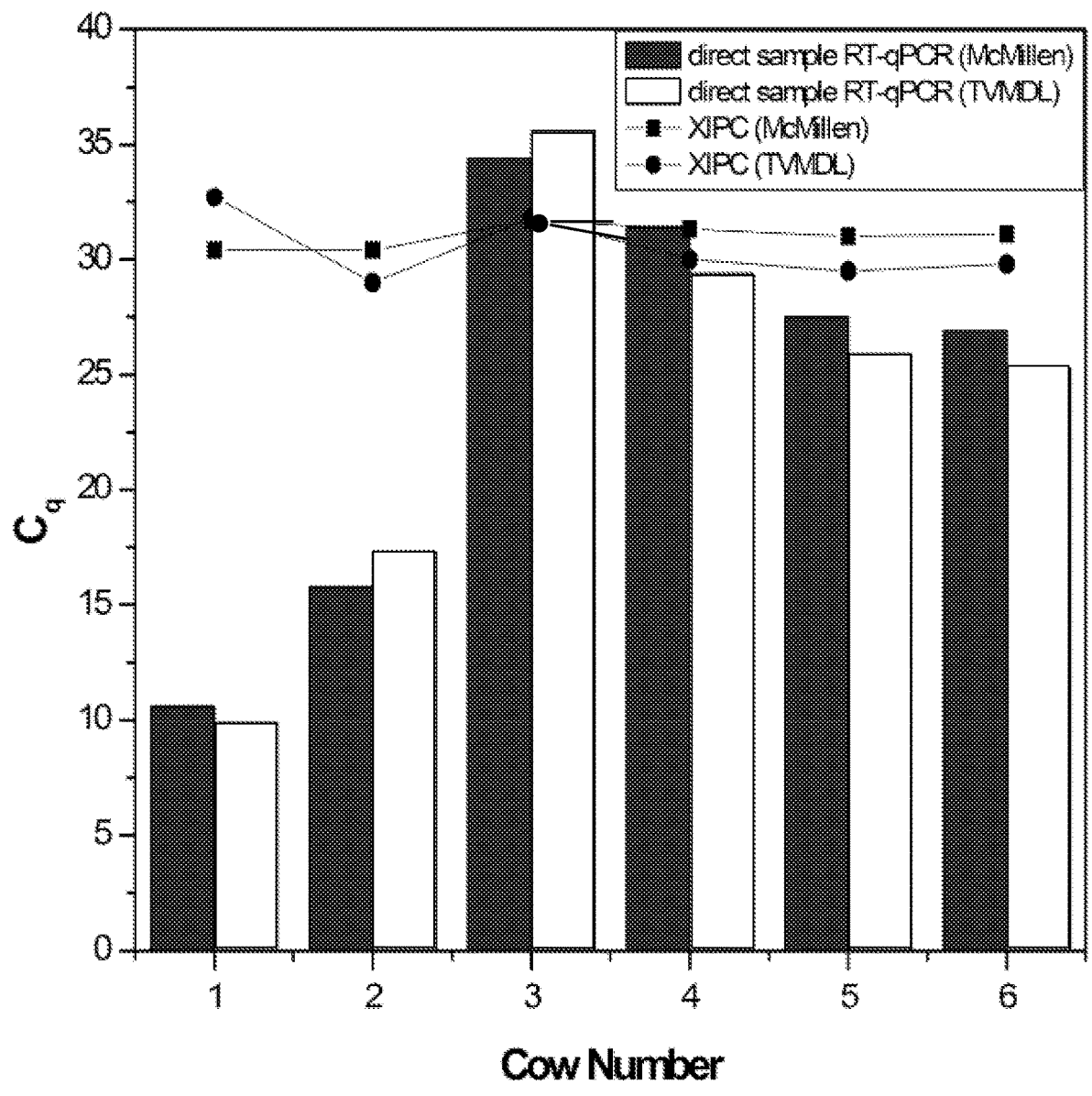
FIG. 5. Direct Sample RT-qPCR $C_q$ values utilizing McMillen and TVMDL assays for six *T. foetus* positive cow cervical mucus/uterine fluid samples. Bars represent the *T. foetus* $C_q$ values for respective assays; dots represent the XIPC $C_q$ value from respective assays for each sample. Cow number 1-3 produced late term abortions; cow number 4-6 were non-bred open replacement additions.

The direct smegma RT-qPCR performance was also evaluated using a small set of cervical mucus and uterine fluid samples collected from cows following abortion or from herds with reproductive issues. Six of the sixteen samples were *T. foetus* positive (Cq range=10.6-34.4 (McMillen assay); Cq range 9.9-35.6 (TVMDL assay); FIG. 5), demonstrating the extended cow diagnostic application of the present invention.

Example 2—Validation of Nucleic Acid Detection Method for *T. vaginalis*

The proof of principle of the invention is also applicable to the human pathogen *Trichomonas vaginalis*, as shown in Table 4. "NA" denotes purified RNA and DNA, "qPCR" denotes PCR targeting the DNA, and "RT-qPCR" below denotes targeting RNA and DNA. The data demonstrate higher sensitivity (6 Cq earlier) with the invention method.

TABLE 4

| *T. vaginalis* | qPCR Cq | RT-qPCR Cq | ΔCq(RT-qPCR-qPCR) |
|---|---|---|---|
| Stock NA | 24.6 | 18.3 | −6.3 |
| (—)10X NA | 28.1 | 22.0 | −6.1 |
| (—)100X NA | 31.8 | 25.5 | −6.4 |

DISCUSSION

Bovine Trichomoniasis is a highly contagious venereal disease with worldwide distribution which causes significant economic loss to the cattle industry. Accurate diagnosis is critical for disease control. Current diagnostic methods are fraught with challenges which prevent timely, economical, reliable, and accurate diagnosis. The challenges include: cost associated with sample collection in InPouch media, inconsistencies in shipment conditions and incubation time and temperature, time burden of incubation, and labor burden of a cumbersome InPouch sample access process. To overcome these challenges, the present invention provides a RT-qPCR test that utilizes direct smegma instead of the InPouch, eliminating the cost of the InPouch, the need for incubation and decreasing time and labor burden for both the submitter and the laboratory. Smegma is collected into a tube and used directly for nucleic acid purification. Thus, without incubation in InPouch media, faster results are enabled, allowing faster movement of animals. These improvements benefit producers, veterinarians, and diagnostic labs in their efforts to control *T. foetus*.

The methods and kits of the present invention significantly improves *T. foetus* detection by providing 5.8 S rRNA RNA detection by RT-qPCR. The 5.8 S rRNA gene (DNA) is highly repetitive (100-2000 copies per cell). Transcription of this gene by RNA polymerase results in a high number of copies of 5.8 S rRNA (up to 20,000 copies per cell). By detecting the RNA, highly improved sensitivity is observed. Furthermore, the present invention eliminates the requirement of InPouch incubation, saving time and money. Furthermore, rapid testing and results are possible, and targeting the coding sequence, RNA, is applicable for detection of other pathogens, as demonstrated for the detection of another venereal disease (human), *Trichomonas vaginalis*, in the example provided.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

We claim:

1. A quantitative polymerase chain reaction (qPCR) method for diagnosing trichomoniasis in a sample, the method comprising:
   receiving the sample;
   extracting nucleic acids from the sample that has not been cultured prior to the extraction of said nucleic acids;
   carrying out a qPCR on the nucleic acids with a primer set comprising a forward primer comprising the nucleotide sequence of SEQ ID NO: 3 and a reverse primer comprising the nucleotide sequence of SEQ ID NO: 4; and
   detecting the PCR amplicon produced in the qPCR by a probe comprising the nucleotide sequence of SEQ ID NO: 6, wherein the probe is conjugated to a marker that provides a detectable signal;
   wherein the presence of the PCR amplicon indicates a positive diagnosis of trichomoniasis.

2. The qPCR method of claim 1, wherein the sample is a biological sample and said sample is not cultured prior to the extraction of said nucleic acids.

3. The qPCR method of claim 2, wherein the sample is a smegma or cervical/uterine fluid sample.

4. The qPCR method of claim 1, further comprising:
   carrying out a second qPCR on the nucleic acids with a second primer set comprising a second forward primer comprising the nucleotide sequence of SEQ ID NO: 1 and a second reverse primer comprising the nucleotide sequence of SEQ ID NO: 2; and
   detecting the second PCR amplicon produced in the second qPCR by a second probe comprising the nucleotide sequence of SEQ ID NO: 5, wherein the second probe is conjugated to a second marker that provides a detectable signal.

5. The qPCR method of claim 4, wherein the second marker conjugated to the probe that provides the second detectable signal is a dye, radioisotope or fluorescent label.

6. The qPCR method of claim 1, wherein the marker conjugated to the probe that provides the detectable signal is a dye, radioisotope or fluorescent label.

7. The qPCR method of claim 1, further comprising carrying out a control qPCR for an exogenous internal positive control polynucleotide and the respective internal positive control primer set comprising a control forward primer and a control reverse primer wherein the control forward primer and the control reverse primer are capable of generating a control PCR amplicon from the exogenous internal positive control polynucleotide.

8. The qPCR method of claim 7, wherein the exogenous internal positive control polynucleotide comprises the nucleotide sequence of SEQ ID NO: 8 and the control forward primer comprises the nucleotide sequence of SEQ ID NO: 9 and wherein the control reverse primer comprises the nucleotide sequence of SEQ ID NO: 10.

9. The qPCR method of claim 1, wherein said sample is obtained from a human, bovine, canine or feline animal.

10. The qPCR method of claim 1, wherein said qPCR is RT qPCR.

11. A kit for the detection of *Tritrichomonas* spp. or *Trichomonas* spp., the kit comprising:
   a primer set comprising a forward primer comprising the nucleotide sequence of SEQ ID NO: 3 and a reverse primer comprising the nucleotide sequence of SEQ ID NO: 4; and
   a probe comprising the nucleotide sequence of SEQ ID NO: 6, wherein the probe is conjugated to a marker that provides a detectable signal.

12. The kit of claim 11, further comprising an exogenous internal positive control polynucleotide and the respective internal positive control primer set comprising a control forward primer and a control reverse primer wherein the control forward primer and the control reverse primer are capable of generating a control PCR amplicon from the exogenous internal positive control polynucleotide.

13. The kit of claim 12, wherein the exogenous internal positive control polynucleotide comprises the nucleotide sequence of SEQ ID NO: 8.

14. The kit of claim 12, wherein the control forward primer comprises the nucleotide sequence of SEQ ID NO: 9 and wherein the control reverse primer comprises the nucleotide sequence of SEQ ID NO: 10.

15. The kit of claim 13, wherein the control forward primer comprises the nucleotide sequence of SEQ ID NO: 9 and wherein the control reverse primer comprises the nucleotide sequence of SEQ ID NO: 10.

16. The kit of claim 11, further comprising a second forward primer comprising the nucleotide sequence of SEQ ID NO: 1 and a second reverse primer comprising the nucleotide sequence of SEQ ID NO: 2 and a second probe comprising the nucleotide sequence of NO: 5, wherein the second probe is optionally conjugated to a second marker that provides a second detectable signal.

17. The kit of claim 16, said kit further comprising an exogenous internal positive control polynucleotide and the respective internal positive control primer set comprising a control forward primer and a control reverse primer wherein the control forward primer and the control reverse primer are capable of generating a control PCR amplicon from the exogenous internal positive control polynucleotide.

18. The kit of claim 17, wherein the exogenous internal positive control polynucleotide comprises the nucleotide sequence of SEQ ID NO: 8 and the control forward primer comprises the nucleotide sequence of SEQ ID NO: 9 and wherein the control reverse primer comprises the nucleotide sequence of SEQ ID NO: 10.

19. The kit of claim 16, wherein the second marker conjugated to the probe that provides the second detectable signal is a dye, radioisotope or fluorescent label.

20. The kit of claim 11, wherein the marker conjugated to the probe that provides the detectable signal is a dye, radioisotope or fluorescent label.

* * * * *

SEQUENCE LISTING

<160> NUMBER OF SEQ ID NOS: 15

<210> SEQ ID NO 1
<211> LENGTH: 21

<212> TYPE: DNA
<213> ORGANISM: Tritrichomonas foetus

<400> SEQUENCE: 1
gcggctggat tagctttctt t 21

<210> SEQ ID NO 2
<211> LENGTH: 16
<212> TYPE: DNA
<213> ORGANISM: Tritrichomonas foetus

<400> SEQUENCE: 2
ggcgcgcaat gtgcat 16

<210> SEQ ID NO 3
<211> LENGTH: 23
<212> TYPE: DNA
<213> ORGANISM: Tritrichomonas foetus

<400> SEQUENCE: 3
gaacgttgca taatgcgata agc 23

<210> SEQ ID NO 4
<211> LENGTH: 26
<212> TYPE: DNA
<213> ORGANISM: Tritrichomonas foetus

<400> SEQUENCE: 4
aacatatatg cgtgttctag caagct 26

<210> SEQ ID NO 5
<211> LENGTH: 16
<212> TYPE: DNA
<213> ORGANISM: Tritrichomonas foetus

<400> SEQUENCE: 5
acaagttcga tctttg 16

<210> SEQ ID NO 6
<211> LENGTH: 24
<212> TYPE: DNA
<213> ORGANISM: Tritrichomonas foetus

<400> SEQUENCE: 6
atctttgaat gcacattgcg cgcc 24

<210> SEQ ID NO 7
<211> LENGTH: 1069
<212> TYPE: RNA
<213> ORGANISM: Artificial Sequence
<220> FEATURE:
<223> OTHER INFORMATION: noninfectious unique artificial antigenomic
sequence (GenBank Accession DQ883679)

<400> SEQUENCE: 7
gggcgaauug gguacaauua ccggguacuu acagcuuguc aauccgcgcu cuuuacaggc 60
cuccugagua acauaggguu aagccacugu uaaagcucug aaacauccuc ggcucccgca 120
aucuugcggu agcaaggaua uacgguauuc uuagagagca ugucaccugc gcuuagaagu 180
ccuugaccug gcaaacauac cguaucuacu agacggacua cagguaacau uugcuugacu 240
uuaguguacc gucagugguu gcugcauaua ggggugcagc ucgcauguuc cggaaauagg 300
gaucaguuau acacuaucgg acgcuuauuu acgucgaccu cuggccgugg gccacccaua 360

-continued

```
auuguucacg auuaagccaa gcuaguuuua acggugagac gugccaaagu uaccaaucau    420
uagcuccggg guacuuugac cgaugcacac cucguaccug cgccuggcug ucggagcaga    480
cuguugaucu accccacagc guaucgaggg uuugaaggcg aaucauaaac cgcaggagag    540
ccuagucaaa uugugggcug ggaaucaccu uucacggaaa ucugccguag caggagguaa    600
auagcugugc ggacaccuaa ucgccucccu uccgagguua gugauggagu guggccgaua    660
gaaucguuca cacaacugug aguacgugac auuauaagca uuacugugcu ucggcguguu    720
augcuaacuu ccuaaccucc gcagaaaucc agggucaucg cgaagguugg gcgcagugga    780
cguagggcgu ugaucuauug ucaagcggga gcccggcagu gaggucguuc aacgaagaua    840
ugguacuaug gcgccgcuga uuauauuuuc ggugaaaggu gaagguuauc ugaugcucgu    900
aagacggcug agccuugcgu cugcguccau cuuucacgau ucucgcacuu uuuagcccaa    960
caguacucug ggaggucgcg cuacaaaaaa aaaaaaaaaa aaaaaaaaaa aaaaaugaaa   1020
cuagcauaac cccuuggggc cucuaaacgg gucuugaggg guuuuuuga               1069
```

```

<210> SEQ ID NO 8
<211> LENGTH: 1069
<212> TYPE: DNA
<213> ORGANISM: Artificial Sequence
<220> FEATURE:
<223> OTHER INFORMATION: noninfectious unique artificial antigenomic
      sequence (GenBank Accession DQ883679)

<400> SEQUENCE: 8

```

```
gggcgaattg ggtacaatta ccgggtactt acagcttgtc aatccgcgct ctttacaggc     60
ctcctgagta acatagggtt aagccactgt taaagctctg aaacatcctc ggctcccgca    120
atcttgcggt agcaaggata tacggtattc ttagagagca tgtcacctgc gcttagaagt    180
ccttgacctg gcaaacatac cgtatctact agacggacta caggtaacat ttgcttgact    240
ttagtgtacc gtcagtggtt gctgcatata ggggtgcagc tcgcatgttc cggaaatagg    300
gatcagttat acactatcgg acgcttattt acgtcgacct ctggccgtgg gccacccata    360
attgttcacg attaagccaa gctagtttta acggtgagac gtgccaaagt taccaatcat    420
tagctccggg gtactttgac cgatgcacac ctcgtacctg cgcctggctg tcggagcaga    480
ctgttgatct accccacagc gtatcgaggg tttgaaggcg aatcataaac cgcaggagag    540
cctagtcaaa ttgtgggctg ggaatcacct ttcacggaaa tctgccgtag caggaggtaa    600
atagctgtgc ggacacctaa tcgcctccct tccgaggtta gtgatggagt gtggccgata    660
gaatcgttca cacaactgtg agtacgtgac attataagca ttactgtgct tcggcgtgtt    720
atgctaactt cctaacctcc gcagaaatcc agggtcatcg cgaaggttgg gcgcagtgga    780
cgtagggcgt tgatctattg tcaagcggga gcccggcagt gaggtcgttc aacgaagata    840
tggtactatg gcgccgctga ttatattttc ggtgaaaggt gaaggttatc tgatgctcgt    900
aagacggctg agccttgcgt ctgcgtccat ctttcacgat tctcgcactt tttagcccaa    960
cagtactctg ggaggtcgcg ctacaaaaaa aaaaaaaaaa aaaaaaaaaa aaaaatgaaa   1020
ctagcataac cccttggggc ctctaaacgg gtcttgaggg gtttttttga              1069
```

```
<210> SEQ ID NO 9
<211> LENGTH: 22
<212> TYPE: DNA
<213> ORGANISM: Artificial sequence
<220> FEATURE:
<223> OTHER INFORMATION: noninfectious unique artificial antigenomic
``` sequence (GenBank Accession DQ883679) primer sequence

<400> SEQUENCE: 9
ttcggcgtgt tatgctaact tc                                              22

<210> SEQ ID NO 10
<211> LENGTH: 17
<212> TYPE: DNA
<213> ORGANISM: Artificial Sequence
<220> FEATURE:
<223> OTHER INFORMATION: noninfectious unique artificial antigenomic
      sequence (GenBank Accession DQ883679) primer sequence

<400> SEQUENCE: 10
ccactgcgcc caacctt                                                    17

<210> SEQ ID NO 11
<211> LENGTH: 24
<212> TYPE: DNA
<213> ORGANISM: Artificial Sequence
<220> FEATURE:
<223> OTHER INFORMATION: noninfectious unique artificial antigenomic
      sequence (GenBank Accession DQ883679) primer sequence

<400> SEQUENCE: 11
ctccgcagaa atccagggtc atcg                                            24

<210> SEQ ID NO 12
<211> LENGTH: 451
<212> TYPE: RNA
<213> ORGANISM: Tritrichomonas foetus

<400> SEQUENCE: 12
gggcgaauug gguaccguua ucuagaggaa ggagaagucg uaacaaggua acgguaggug 60
aaccugccgu uggaucaguu ucguuaauaa uuacaaacau auuuuuuuaa ugucuauaac 120
uauuuauaca aaauuaaaca cauaaucuaa aaaauuuaga ccuuaggcaa uggaugucuu 180
ggcuucuuac acgaugaaga acguugcaua augcgauaag cggcuggauu agcuuucuuu 240
gcgacaaguu cgaucuuuga augcacauug cgcgccguuu uagcuugcua gaacacgcau 300
auauguuaca guaacccaua uuaauuuaau accaaauucu cuuuuuaagc aaaagagcga 360
aaaauaaaua uguauuaaca aaaggguucu gucucauaua ggaagacccg cugaacugaa 420
gcaucucauu aagcggagga aaagaaacua a 451

<210> SEQ ID NO 13
<211> LENGTH: 451
<212> TYPE: DNA
<213> ORGANISM: Tritrichomonas foetus

<400> SEQUENCE: 13
gggcgaattg ggtaccgtta tctagaggaa ggagaagtcg taacaaggta acggtaggtg 60
aacctgccgt tggatcagtt tcgttaataa ttacaaacat attttttaa tgtctataac 120 tatttataca aaattaaaca cataatctaa aaaatttaga ccttaggcaa tggatgtctt 180
ggcttcttac acgatgaaga acgttgcata atgcgataag cggctggatt agctttcttt 240
gcgacaagtt cgatctttga atgcacattg cgcgccgttt tagcttgcta gaacacgcat 300
atatgttaca gtaacccata ttaatttaat accaaattct ctttttaagc aaaagagcga 360
aaaataaata tgtattaaca aaagggttct gtctcatata ggaagacccg ctgaactgaa 420
gcatctcatt aagcggagga aaagaaacta a 451

```
<210> SEQ ID NO 14
<211> LENGTH: 15
<212> TYPE: DNA
<213> ORGANISM: Artificial Sequence
<220> FEATURE:
<223> OTHER INFORMATION: primer sequence from T7 promoter
      (bacteriophage) - viral DNA

<400> SEQUENCE: 14
gggcgaattg ggtac                                                        15

<210> SEQ ID NO 15
<211> LENGTH: 54
<212> TYPE: DNA
<213> ORGANISM: Artificial Sequence
<220> FEATURE:
<223> OTHER INFORMATION: primer sequence from T7 terminator
      (bacteriophage) - viral DNA

<400> SEQUENCE: 15
tgaaactagc ataaccccrt ggggcctcta aacgggtctt gagggggtttt ttga            54
```